United States Patent
Fette et al.

(10) Patent No.: US 8,975,075 B2
(45) Date of Patent: Mar. 10, 2015

(54) HEMOSTATIC DEVICE

(71) Applicant: ACell, Inc., Columbia, MD (US)

(72) Inventors: Clay Fette, Severna Park, MD (US);
Abram Janis, Elkridge, MD (US);
Benjamin Kibalo, Columbia, MD (US)

(73) Assignee: ACell, Inc., Columbia, MD (US)

( * ) Notice: Subject to any disclaimer, the term of this patent is extended or adjusted under 35 U.S.C. 154(b) by 0 days.

(21) Appl. No.: 14/508,520

(22) Filed: Oct. 7, 2014

(65) Prior Publication Data

US 2015/0037416 A1 Feb. 5, 2015

Related U.S. Application Data

(62) Division of application No. 13/706,987, filed on Dec. 6, 2012, now Pat. No. 8,895,304.

(60) Provisional application No. 61/568,946, filed on Dec. 9, 2011.

(51) Int. Cl.
| | | |
|---|---|---|
| *C12N 5/00* | (2006.01) |
| *C12N 5/02* | (2006.01) |
| *A01N 63/00* | (2006.01) |
| *A01N 65/00* | (2009.01) |
| *A61F 2/00* | (2006.01) |
| *A61K 9/14* | (2006.01) |
| *A61B 17/08* | (2006.01) |
| *A61D 1/00* | (2006.01) |
| *A61L 27/36* | (2006.01) |
| *A61L 27/58* | (2006.01) |
| *A61L 27/54* | (2006.01) |

(52) U.S. Cl.
CPC ............. *A61L 27/3666* (2013.01); *A61L 27/58* (2013.01); *A61L 27/54* (2013.01); *A61L 27/3633* (2013.01); *A61L 2430/22* (2013.01); *A61L 2400/04* (2013.01); *A61L 2300/418* (2013.01)
USPC .......... 435/395; 424/93.7; 424/423; 424/484; 606/213

(58) Field of Classification Search
None
See application file for complete search history.

(56) References Cited

U.S. PATENT DOCUMENTS

| | | | |
|---|---|---|---|
| 4,902,508 | A | 2/1990 | Badylak et al. |
| 5,554,389 | A | 9/1996 | Badylak et al. |
| 6,576,265 | B1 | 6/2003 | Spievack |
| 6,793,939 | B2 | 9/2004 | Badylak |
| 8,119,160 | B2 | 2/2012 | Looney |
| 2003/0133916 | A1 | 7/2003 | Spievack |
| 2005/0049637 | A1 | 3/2005 | Moriss et al. |
| 2008/0181950 | A1 | 7/2008 | Bates et al. |
| 2008/0293919 | A1 | 11/2008 | Kaplan et al. |
| 2009/0118166 | A1 | 5/2009 | Badylak |
| 2010/0233235 | A1 | 9/2010 | Matheny et al. |
| 2010/0297212 | A1 | 11/2010 | Badylak |

FOREIGN PATENT DOCUMENTS

| | | |
|---|---|---|
| EP | 1659919 | 5/2006 |
| WO | 2005016116 | 2/2005 |

OTHER PUBLICATIONS

International Preliminary Report on Patentability for International Application No. PCT/US2012/068193, dated Jun. 10, 2014 (6 pages).
MatriStem MicroMatrix®-based Haemostatic Dressings are Effective in Acute Haemorrhage. (2011) Kibalo et al. Available online, http://abstracts.conferencestrategists.com/resources/1165/2805/pdf/TERMIS2011_0173.pdf.
Advanced Vascular Dynamics: A leader in post catheterization hemostasis, 2pgs. (2011) Advanced Vascular Dynamics Brochure.
Section II, Therapeutic Strategies—Surgical Perspectives to Control Bleeding in Trauma; vol. 18. No. 1, 2008 http://www.itaccs.com/traumacare/archive/2008_vol18_no1/Surgical_Perspectives_Control_Bleeding_Itaccs_vol.18no1-5.pdf.
Beattie et al. "Chemoattraction of Progenitor Cells of Remodeling Extracellular Matrix Scaffolds" Tissue Engineering: Part A, vol. 15, No. 5, 2009 © Mary Ann Liebert, Inc., DOI: 10.1089/ten.tea.2008.0162, pp. 1119-1125.
Brown et al. "The Basement Membrane Component of Biologie Scaffolds Derived from Extracellular Matrix" Tissue Engineering: vol. 12, No. 3, 2006, © Mary Ann Liebert, Inc., pp. 519-526.
Voytik-Harbin et al. "Small Intestinal Submucosa: A Tissue-Derived Extracellular Matrix That Promotes Tissue-Specific Growth and Differentiation of Cells in Vitro" Tissue Engineering: vol. 4, No. 2, 1998, © Mary Ann Liebert, Inc., pp. 157-174.
Pusateri et al. "Making Sense of the Preclinical Literature on Advanced Hemostatic Products" The Journal of Trauma® Injury, Infection, and Critical Care, 2006; 60, pp. 674-682.
Tottey et al. "Extracellular Matrix Degradation Products and Low-Oxygen Conditions Enhance the Regenerative Potential of Perivascular Stem Cells" Tissue Engineering: Part A, vol. 17, Nos. 1 and 2, 2011, © Mary Ann Liebert, Inc., DOI: 10.1089/ten.tea.2010.0188, pp. 37-44.
Brennan et al. "Antibacterial Activity within Degradation Products of Biological Scaffolds Composed of Extracellular Matrix" Tissue Engineering: vol. 12, No. 10, 2006, © Mary Ann Liebert, Inc., pp. 2949-2955.
Bergfeld "Androgenetic Alopecia: An Autosomal Dominant Disorder" The American Journal of Medicine, vol. 98 (suppl 1A) Jan. 16, 1995, pp. 1A-95S-1A-98S.

(Continued)

*Primary Examiner* — Chris R Tate
*Assistant Examiner* — Douglas F White
(74) *Attorney, Agent, or Firm* — Burns & Levinson LLP

(57) ABSTRACT

A hemostatic device, method of making, and method of using for internal and external applications to wounds in the body of a patient to induce hemostasis at an anatomical site.

16 Claims, 2 Drawing Sheets

(56) References Cited

OTHER PUBLICATIONS

Chun et al. "Identification and characterization of bioactive factors in bladder submucosa matrix" Elsevier Ltd., ScienceDirect, Biomaterials 28 (2007) pp. 4251-4256, DOI: 10.1016/j.biomaterials.2007.05.020.

Kelly et al. "Increased Myocyte Content and Mechanical Function Within a Tissue-Engineered Myocardial Patch Following Implantation" Tissue Engineering: Part A, vol. 15, No. 8, 2009, © Mary Ann Liebert, Inc., DOI: 10.1089/ten.tea.2008.0430, pp. 2189-2201.

Mase et al. "Clinical Application of an Acellular Biologic Scaffold for Surgical Repair of a Large, Traumatic Quadriceps Femoris Muscle Defect" Case Report, Jul. 2010, vol. 33, No. 7, p. 511, OrthoSuperSite.com/view.aspx?rID=65583.

Gilbert et al. "Production and characterization of ECM powder: implications for tissue engineering applications" Elsevier Ltd., ScienceDirect, Biomaterials 26 (2005) pp. 1431-1455, DOI: 10.1016/j.biomaterials.2004.04.042.

Reing et al. "Degradation Products of Extracellular Matrix Affect Cell Migration and Proliferation" Tissue Engineering: Part A, vol. 15, No. 3, 2009,© Mary Ann Liebert, Inc., DOI: 10.1089/ten.tea.2007.0425, pp. 605-614.

Sarikaya et al. "Antimicrobial Activity Associated with Extracellular Matrices" Tissue Engineering: vol. 8, No. 1, 2002, © Mary Ann Liebert, Inc., pp. 63-71.

Rhee et al. "QuikClot Use in Trauma for Hemorrhage Control: Case Series of 103 Documented Uses" The Journal of TRAUMA® Injury, Infection, and Critical Care, 2008; 64, pp. 1093-1099.

Badylak et al. "SnapShot: Biologic Scaffolds for Constructive Tissue Remodeling" McGowan Institute for Regenerative Medicine, University of Pittsburgh, Pittsburgh, PA., and Department of Surgery, University of Pittsburgh, Pittsburgh, PA, Biomaterials 2011 32(1) p. 316-9.

Badylak, Stephen F., Special Article "Regenerative Medicine and Developmental Biology: The Role of the Extracellular Matrix." The Anatomical Record (Part B: New Anat.) 287B:36-41, 2005, pp. 36-41, © 2005 Wiley-Liss, Inc.

Badylak, Stephen F., DVM., Ph.D., MD "Extracellular Matrix As a Scaffold for Tissue Engineering in Veterinary Medicine: Applications to Soft Tissue Healing." Clinical Techniques in Equine Practice, pp. 173-181, © 2004 Elsevier Inc.

Badylak, Stephen F. et al., "Immune Response to Biologic Scaffold Materials." McGowan Institute for Regenerative Medicine, University of Pittsburgh, PA, NIH Public Access Author Manuscript Published in final edited form as *Semin Immunol*. Apr. 2008, 20(2): 109-116, doi:10.1016/j.smim.2007.11.003, pp. 1-13.

Xie, Hua et al., "Long-term outcomes of a chitsosan hemostatic dressing in laparoscopic partial nephrectomy." Oregon Center for Regenerative Medicine, Providence St., Vincent Medical Center, Portland, Oregon, CVPath Institute, Gaithersburg, Maryland, Journal of Biomedical Materials Research B: Applied Biomaterials, Feb. 2012, vol. 100B, Issue 2, pp. 432-436.

Badylak, Stephen F., The extracellular matrix as a scaffold for tissue reconstruction; (2002) 13 ESCDBO 5, pp. 377-383, vol. 13, No. 5 ISSN: 1084-9521, Department of Biomedical Engineering, Purdue University, Room 204, 1296 Potter Building, West Lafayette, IN.

Janis, Abram Daved, et al., "Structural Characteristics of Small Intestinal Submucosa Constructs Dictate In Vivo Incorporation and Angiogenic Response." Journal of Biomaterials Applications, vol. 26, May 2012, pp. 1013-1033.

Hodde, Jason, et al. "Effects of Sterilization on an extracellular matrix scaffold: Part I. Composition and matrix architecture." J. Mater Sci: Mater Med (2007) 18:537-543, DOI 10.1007/s10856-2300-x.

Agrawal, Vineet, B.S.E., et al., "Recruitment of Progenitor Cells by an Extracellular Matrix Cryptic Peptide in a Mouse Model of Digit Amputation." Tissue Enginerring Part A, vol. 17, Nos. 19 and 20, 2011, © Mary Anne Liebert, Inc., DOI: 10.1089/ten.tea.2011.0036, pp. 2435-2443.

Machingal, Masood A. et al., "A Tissue-Engineered Muscle Repair Construct for Functional Restoration of an Irrecoverable Muscle Injury in a Murine Model." Tissue Enginerring Part A, vol. 17, Nos. 17 and 18, 2011, © Mary Ann Liebert, Inc., DOI: 10.1089/ten.tea.2010.0682, pp. 2291-2303.

Nieponice, Alejandro, MD, et al., "An extracellular matrix scaffold for esophageal stricture prevention after circumferential EMR." Original Article: Experimental Endoscopy, vol. 69, No. 2: 2009, Gastrointestinal Endoscopy, pp. 289-296.

Daly, Kerry A., et al., "A Rabbit Model of Peripheral Compartment Syndrome with Associated Rhabdomyolysis and a Regenerative Medicine Approach for Treatment." Tissue Enginerring Part C, vol. 17, No. 6, 2011, © Mary Ann Liebert, Inc., DOI: 10.1089/tea.tec.2010.0699, pp. 631-640.

Badylak, Stephen, DVM, PhD, MD, et al. "Naturally Occurring Extracellular Matrix as a Scaffold for Musculoskeletal Repair." Clinical Orthopedics and Related Research, No. 367S, pp. S333-S343, © 1999 Lippincott Williams & Wilkins, Inc.

Kimmel, Howard, DPM[2] et al., Case Study: "The Clinical Effectiveness in Wound Healing with Extracellular Matrix Derived from Porcine Urinary Bladder Matrix: A Case Series on Severe Chronic Wounds." Journal of the American College of Certified Wound Specialists (2010) 2, pp. 55-59, © 2010 Elsevier, Inc.

Donald O. Freytesa et al. Preparation and rheological characterization of a gel form of the porcine urinary bladder matrix. vol. 29, Issue 11, Apr. 2008, pp. 1630-1637.

Medberry CJ et al. Resistance to infection of five different materials in a rat body wall model. J Surg Res. Mar. 2012;173(1):38-44, doi: 10.1016/j.jss.2010.08.035. Epub Sep. 17, 2010.

Fette, Clay et al., The International Search Report and The Written Opinion of The International Searching Authority, dated Feb. 14, 2013 from corresponding international application PCT/US2012/068193, Filed on Dec. 6, 2012, pp. 1-10.

HEMOSTATIC DEVICE

CROSS REFERENCE TO RELATED APPLICATIONS

This application is a divisional application of U.S. patent application Ser. No. 13/706,987, filed Dec. 6, 2012, which claims priority to and the benefit of U.S. Provisional Application No. 61/568,946, filed on Dec. 9, 2011. This application is related to U.S. patent application Ser. No. 14/161,826 filed Jan. 23, 2014, now U.S. Pat. No. 8,835,174, issued Sep. 16, 2014. U.S. patent application Ser. No. 14/161,826 is a divisional of U.S. patent application Ser. No. 13/706,987.

TECHNICAL FIELD OF THE INVENTION

The invention is directed to a hemostatic device such as a topical or implanted hemostatic device that may be applied to an internal or external anatomic site in a patient to assist hemostasis, and methods of making and methods of using the hemostatic device.

BACKGROUND

Hemostasis is the means by which blood loss is terminated from an injured artery, vein, or damaged parenchyma. The process of hemostasis uses circulating proteins such as coagulation factors, cell membranes, and the lining of the blood vessels called endothelium. Hemostasis as a process is highly complex, begins with vasoconstriction, local mediators, platelet adherence to the vessel wall, aggregation of platelets, and the release of platelet granules. At the same time, the coagulation cascade is triggered with the two traditional divisions of the coagulation process—the intrinsic and extrinsic pathway processes that are measured by clotting time. Ultimately these processes lead to blood clotting which, along with platelet aggregation, seal the injured artery or vein.

Following trauma, such as may be recognized in military medical care or traditional civilian trauma, the physician must identify all sources of blood loss from the patient such as the skin surface, thorax, abdomen, pelvis or retroperitoneum, and fractured limbs or skull. Often traumatized patients also suffer from complications such as hypotension, acidosis, hypothermia, organ dysfunction and severe shock. Under such conditions, rapid hemostasis is critical and must begin even before blood transfusion is available. Accordingly, topical and implanted hemostatic agents have gained importance in all causes of trauma including trauma in the military field.

Surgical intervention due to diseased or damaged tissues such as the surgical excision or removal of tissue can result in blood loss due to severed vessels. Current standard of care includes thermal coagulation and closure of the vessels and tissue which can result in thermal damage to the site and surrounding tissues and impede repair and function. Achieving non-thermal hemostasis at a surgical site in a patient could result in improved healing outcomes.

The properties of an ideal topical hemostatic agent include rapid hemostasis, easy application both internally and externally, suture strength, bioresorption, manipulability, minimal adverse tissue reaction, long shelf-life, and low cost. Pusateri et al. Making sense of the preclinical literature on advanced hemostatic products. J Trauma 60(3): 674-82 (2006). An additional desirable characteristic of a hemostatic device is that it has anti-microbial properties.

Numerous topical hemostatic agents have been developed but all of these agents have substantial drawbacks. Although the last decade has been a turning point in the treatment of acute traumatic hemorrhage with the advent of several new hemostatic dressings, an unacceptably high proportion of pre-evacuation combat deaths in Operation Iraqi Freedom and Operation Enduring Freedom are attributed to uncontrolled hemorrhage. Emergency Medicine Review: 2005, p. 1-4. These currently deployed technologies have persistent problems: QuikClot zeolite granular dressing (QC, Z-Medica) can cause exothermic reaction at the application site (J. Trauma, 2008. 64(4): p. 1093-9) and may be ineffective in bleeding fields; chitosan hemostatic dressing (HC, Hemcon) and Rapid Deployment Hemostat (RDH, Marine Polymer Technologies) are non-bioabsorbable, J. Trauma, 2006. 60(3): p. 674-82. None of these dressings are currently FDA cleared for internal use. Collagen sponges, and gelatin sponges may not result in enhanced platelet aggregation and may not have a significant impact on clotting time. The potentially implantable dry fibrin sealant dressing (DFSD, American Red Cross) is expensive, regulated as a biologic, and is currently only approved for investigational use. None of the current topical hemostatic agents are believed to have antimicrobial properties.

Urinary bladder matrix (UBM) is a well-characterized scaffold that was developed for site-specific tissue repair of various tissues and was found to have anti-microbial in vitro as well as regenerative properties.

UBM is derived from the extracellular matrix of the urinary bladder of pigs. Other animals, such as ruminants, are also suitable sources of UBM. UBM, in contrast to other ECMs, includes the epithelial basement membrane and other layers of the wall of the urinary bladder and is composed of at least collagen types I-IV and VII. Collagen VII is specifically of epithelial basement membrane origin. Other components of UBM of porcine origin include glycosaminoglycans, fibronectin, laminin, elastin, and the following growth factors: vascular endothelial growth factor (VEGF), basic fibroblast growth factor (FGF-2), and connective tissue growth factor (CTGF). K A Kentner & A D Janis, Quantification of FGF-2, VEGF, & GAGs in MatriStem MicroMatrix UBM Biomaterial. BMES 2011 Fall Meeting, Hartford, Conn., Oct. 12-15, 2011. K A Kentner, K A Stuart & A D Janis. Differential release of growth factor from MatriStem® urinary bladder matrix (UBM) products. Society for Biomaterials 2012 Fall Symposium, New Orleans La., Oct. 4-6, 2012. A C Phipps, K A Kentner, K A Stuart, B T Kibalo and A D Janis. Tunable mechanical, structural and biological properties of urinary bladder matrix (UBM) biomaterials. BMES Annual Fall Meeting, Atlanta, Ga., Oct. 24-27, 2012.

Extensive preclinical studies have demonstrated the efficacy of UBM in a wide range of applications, including myocardial repair, esophageal reconstruction, thoracic wall repair, urinary incontinence, penile tunics repair, orthopedics, amputated digit remodeling, and tympanoplasty. UBM was observed to gradually be replaced with implant site-appropriate host tissue following infiltration of the UBM implant by progenitor cells (Tissue Eng. Part A. 2009. 15(5): p. 1119-25), a mechanism of action that has been well characterized in studies of similar ECM-derived scaffolds in vivo. Degradation products of UBM have been demonstrated to have antibacterial activity in vitro (Tissue Eng. 2002. 8(1) p. 63-71; Tissue Eng. 2006. 12(10): p. 2949-55) and in vivo. Medberry et al., J. Surg. Res. 2010.

UBM (MatriStem®, ACell Inc., Columbia Md.) was FDA cleared in 2002 as a medical device and is currently marketed for indications ranging from topical use in cutaneous wounds (J. Am. Coll. Cert. Wound Spec. 2010. 2(3): p. 55-69) and burns to implanted plastic and hernia surgery repair. Wound Repair. Regen. 2011. 19: p. A54, UBM is currently commercially available as powder, lyophilized sheets, and vacuum-pressed multilaminate sheets, and proof of concept gel formulations of ECM have been described. Biomaterials. 2008. 29(11): p. 1630-7; Tissue Eng. 1998, 4(2): p. 157-174.

SUMMARY OF THE INVENTION

As used herein, ECM means a devitalized extracellular matrix material derived from the extracellular matrix of one or more layers of an epithelial tissue. UBM, described above and in U.S. Pat. No. 6,576,265, incorporated by reference herein in its entirety, SIM (small intestinal matrix) described in U.S. Pat. No. 6,576,265, SIS described in U.S. Pat. No. 4,902,508 incorporated by reference, UBS, described in U.S. Pat. No. 5,554,389 incorporated by reference herein in its entirety, LBM described in U.S. Pat. No. 6,793,939 incorporated by reference herein in its entirety, parenchymatous ECMs described in U.S. Ser. No. 10/337,152 incorporated by reference herein in its entirety and Ser. No. 12/851,646 incorporated by reference herein in its entirety, and conditioned ECMs described in U.S. Ser. No. 12/351,757 incorporated by reference herein in its entirety are all examples of ECMs.

As use herein, basement membrane means the epithelial basement membrane, a sheet-like matrix that underlies epithelial cells of the epithelium of an epithelial tissue and separates the epithelial cells from the underlying stroma of epithelial tissue layers, the tunica propria, for example, that are abluminal to the epithelium.

As used herein, native configuration refers to a devitalized extracellular matrix material derived from a native epithelial tissue in which components of a native ECM, for example, a plurality of collagen types native to the epithelial tissue, such as types I, II, III, IV and VII, remain substantially in their native orientation, collagen chain lengths, collagen bundles, and relationship to one another in the extracellular matrix material, thereby substantially maintaining their natural three dimensional architecture and structure as it exists in the host tissue.

As used herein, topical means on the surface of an external tissue of the body, e.g., topical hemostasis arrests bleeding from a vessel on the surface of the skin or exposed subcutaneous tissues.

As used herein, hemostasis means termination of blood loss from an artery, or vein, including but not limited to capillaries and leakage or diffuse blood loss from a tissue or an organ.

As used herein, bleeding shall mean release of blood from the intravascular space or injured parenchymal organ, e.g., the surface of the liver.

As used herein implanted shall mean placed at an internal site in a patient's body and left at the implantation site for one week to 12 months, or as long as up to 6 months to 12 months when permanently implanted and, optionally, bioresorbed.

As used herein, non-cross linking applies to processing tissues before sterilization in the absence of chemical cross-linking agents, thermal cross-linking, and/or cross-linking with visible/ultra violet radiation.

In general, in one aspect the invention relates to a method for assisting hemostasis. The method comprises applying a bioresorbable hemostatic device to a site of bleeding in the body of a patient. The bioresorbable hemostatic device comprises a compressed, particularized, dehydrated extracellular matrix material (ECM) comprising hemostatic properties and extracellular matrix (ECM) components isolated in their native configuration that are derived from an epithelial tissue. In one embodiment, the ECM further comprises epithelial basement membrane and includes one or more layers of the epithelial tissue selected from the group consisting of, for example, tunica muscularis mucosa, tunica propria, tunica submucosa, and tunica muscularis. The bioresorbable hemostatic device substantially arrests blood flow at a rate that exceeds hemostasis that occurs in the absence of a hemostatic device at the site of the bleeding vessel.

In general, in another aspect, the invention relates to a composition and method of making the composition. The composition is a compressed, and/or dehydrated, particularized, extracellular matrix material (ECM) comprising non-cross-linked ECM components isolated in their native configuration. The non-cross-linked ECM components are selected from the group consisting of collagen type IV, collagen type VII, glycosaminoglycans, fibronectin, and laminin. In one embodiment, the ECM comprises epithelial basement membrane and one or more layers of an epithelial tissue selected from the group consisting of, for example, tunica muscularis mucosa, tunica propria, tunica submucosa, and tunica muscularis derived from a mammalian epithelial tissue.

BRIEF DESCRIPTION OF THE FIGURES

These embodiments and other aspects of the invention will be readily apparent from the detailed description below and the appended drawings, which are meant to illustrate and not to limit the invention. The drawings are not to scale and emphasis instead is generally being placed on illustrating the principles of the invention.

Figure 1:
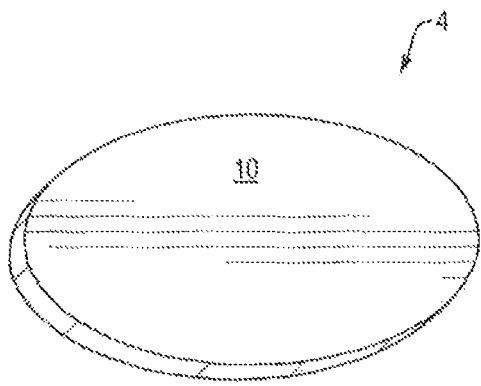
FIG. 1 illustrates a perspective view of the hemostatic device according to one embodiment of the invention.

The invention described herein solves the problem not yet addressed by present topical hemostatic agents by providing a device that induces rapid hemostasis, is bioresorbable, manipulatable, inexpensive, implantable, and bioactive, has a prolonged shelf life, is easily applied both to external and internal wounds while inducing minimal adverse tissue reaction, performs as a tissue regenerative scaffold implanted at the earliest stages (hemostasis) of wound repair, restoration or remodeling and has anti-microbial properties.

DESCRIPTION

In one aspect, the invention is a method of making a topical hemostatic device for internal and external topical hemostatic applications. In one embodiment of the invention, the topical hemostatic device, according to the invention, includes a thin, typically less than 10 mm thick, substantially disc- or rectangular-shaped wafer-like material that is made from devitalized native extracellular matrix of a mammalian epithelial tissue. In a preferred embodiment, the hemostatic device is made from a devitalized native extracellular matrix of a mammalian epithelial tissue and comprises epithelial basement membrane, for example, UBM described above. The ECM of the hemostatic device may include additional layers of the mammalian epithelial tissue including for example, tunica propria, tunica muscularis mucosa, tunica submucosa, tunica muscularis, tunica serosa, and/or a combination of the above.

A method of making UBM is described in U.S. Pat. No. 6,576,265. Briefly, the urinary bladder is removed from a mammal, e.g., pig, sheep, or cow, and the bladder wall is delaminated from the luminal epithelial cells by, for example, but not limited to, soaking the urinary bladder in a hypertonic saline solution for 10 minutes to 120 minutes. Soaking removes the epithelial cells from the underlying epithelial basement membrane. The layers of the epithelial tissue that remain after this initial step are the epithelial basement membrane and all of the layers abluminal to the epithelial basement membrane, i.e., at least the tunica propria, tunica submucosa, tunica muscularis and tunics serosa. One or more tissue layers, for example, tunica propria, tunica muscularis mucosa, tunica submucosa, tunica muscularis and tunica serosa are selectively removed by mechanical abrasion and/or enzymatic or other mild chemical treatment to form the UBM matrix.

After the one or more abluminal layers are selectively removed from the urinary bladder or other epithelial tissue, the resulting matrix includes the epithelial basement membrane lining the luminal surface of the matrix and from which epithelial cells and cellular elements are removed, and one or more tissue layers, for example, tunics muscularis mucosa, tunica propria, tunics submucosa, tunica muscularis and tunica serosa abluminal to the epithelial basement membrane.

According to one embodiment of the invention, the hemostatic device is made by particularizing UBM, or particularizing any other ECM such as UBS, SIS, LBM, and SIM. The description that follows for making the hemostatic device with respect to UBM according to the invention is merely exemplary and is not intended to limit the scope of the invention to merely UBM but may be used for other ECMs such as, but not limited to, UBS, SIS, LBM and SIM.

According to one embodiment of the invention, the hemostatic device may be made as described in: B T Kibalo & A D Janis, MatriStem™ MicroMatrix™-based hemostatic dressings are effective in acute haemorrhage. TERMIS-NA 2011 Conference, Houston Tex. Dec. 11-14, 2011; http://abstracts.conferencestrategists.com/resources/1165/2805/pdf/TERMIS2011_0173.pdf, incorporated by reference herein in its entirety.

Briefly, the particulate ECM product, particularized UBM, for example, is manufactured by grinding/milling or otherwise performing a size reduction process to UBM material typically originally provided in sheet form. The resulting particulate can be any desired range of particle size and density for example in the range of about 1-1000 microns, 200-700 microns, preferably about 300-600 microns, more preferably about 400 microns. In one embodiment, the particulates are compressed together in a mold or form under vacuum pressing or lyophilization conditions to form a three dimensional construct hemostatic device 4.

For example, referring to FIG. 1, the three-dimensional construct 4, may be a disc 10 or a planar rectangular shape. This construct can be further or simultaneously modified, illustrated in FIG. 2, for example, by incorporating a backing sheet form 20 of ECM material, e.g., a sheet of UBM, SIS, UBS, SIM, or LBM, onto the surface of the molded three-dimensional UBM construct 10 that in one embodiment does not contact the site of bleeding, to form the hemostatic device 4. The added backing sheet 20 assists in preventing blood from passing through the hemostatic device when applied to a bleeding site, and to keeping blood contact contained to the molded particulate portion of the hemostatic device. The shapes of the wafer and the backing sheet are not limited to those illustrated in the figures but may be shape-adapted to fit the particular tissue application. This backing also allows securement of the hemostatic device to the site of injury.

In one embodiment of the invention, for example, UBM powder (particulate material), for example, is compressed into a wafer about 1 cm×1 cm×2 mm to about 4 cm×4 cm×4 mm, preferably 2 cm×2 cm×4 mm, dehydrated under a vacuum and optionally joined to a 1 to 6 layer UBM sheet backing, preferably a two layer UBM sheet backing. ECMs other than UBM may alternatively be applied as the sheet backing to a construct such as a wafer made from UBM. The advantage of an ECM backing sheet is because of its enhanced hemostatic properties compared to other materials and its capacity to improve deployability and allow securement of the hemostatic device to the site of injury.

A sheet is preferable for cost considerations and ease of manufacturing.

In one embodiment, the ECM particulate, UBM, for example, is typically in the range of about 0-1000 microns, preferably in the range of about 300-600 microns, more preferably in the range of about 400 microns, although specific particle size ranges will likely be used for various applications based on the size of the hemostatic device or the type of tissue where the hemostatic device will be implanted.

According to another embodiment, the hemostatic device of the invention is made by first making a gel of ECM (digesting the ECM into gel form) and then lyophilizing the gel in a mold to make a wafer.

According to another embodiment, the hemostatic device of the invention includes a gel. For example, ECM material, such as UBM, may be enzymatically digested to convert the particulate/sheet form of UBM into a gel-form material. Digestion is tailored to produce a range of concentration, e.g. in the range of 1 mg/mL to 200 mg/mL, preferably 5-150 mg/mL, most preferably 15-100 mg/mL. In one embodiment, the UBM or other ECM material is digested completely into a gel-form. Alternatively, UBM is partially digested, resulting in a hemostatic device that contains incompletely digested particulate UBM that is suspended in a gel-form material resulting from the digestion of the remainder of the UBM.

In other embodiments, the hemostatic device is made by combining a gel form with a particulate form to make a wafer. The gel may be introduced into a mold with or without particulate forms and cross-linked in the mold to make a wafer. Cross-linking may be achieved with an aldehyde based cross-linker such as glutaraldehyde. Alternative means of cross-linking include thermal energy, ultra-violet light, methylene blue and certain sugar-based cross-linkers such as a saccharide, e.g. glucose, galactose or a disaccharide, e.g. lactose, sucrose.

In yet another embodiment, the device can be all particulate where part of the wafer is compressed into a different density than another part of the wafer, thus forming a sheet, so that one side of the device is more porous than the other side of the device. Similar to the particulate wafer/sheet backed embodiment described above, this embodiment wicks blood into the more porous part of the wafer having the larger surface area to promote hemostasis, while the more dense sheet-like portion of the wafer functions as a physical barrier to blood passing unimpeded through the hemostatic device. The denser sheet-like portion of the wafer may be used as the backing sheet described above.

In yet another embodiment, differing gel form hemostatic devices according to the invention may be made by crosslinking an ECM such as UBM to form a sponge-like or foam material. In another embodiment, the gel is dehydrated (such as via lyophilization) to form a sponge-like or foam material hemostatic device. Additionally, the sponge or foam material may be further combined with particulate UBM or other ECMs and crosslinked or lyophilized to form another type of sponge or foam form material.

In still another embodiment, gel, foam, or sponge form hemostatic devices according to the invention may be partially or totally enveloped by a sheet, container, moldable or pliable material of UBM or other ECM material.

Any of the particulate, gel, foam, or sponge form hemostatic devices may be combined with other biocompatible, and bioresorbable, filler type materials such as, but not limited to collagen, such as purified collagen, mineral material, calcium, magnesium or phosphorous, for example, and for bone applications, hyaluronic acid, biodegradable polymers, and combinations of the above.

In yet another embodiment, the hemostatic device according to the invention comprises a bioresorbable polymer lattice. The lattice is filled with an ECM having hemostatic properties, e.g., UBM gel, foam, or powder, or, alternatively, incorporated with an ECM material such that all interstitial spaces of the lattice work are filled and/or all surfaces of the lattice work are coated with an ECM material. In another embodiment of the invention, a porous material, or combinations of a lattice work and porous material are treated with UBM in the same way as the lattice work. Alternatively, a non-ECM construct that has a structure including interstitial space or pore space is combined with ECM gel, foam, or powder such that the ECM material fills the interstitial or pore space. In yet another embodiment, a non-ECM construct that has a structure including interstitial space or pore space is combined with ECM gel, foam, or powder such that the ECM material coats the surface of the interstitial or pore space.

In another aspect, the invention is a topical method for inducing and accelerating hemostasis using the topical hemostatic devices described above. The method for using the hemostatic device of the invention includes internal and external topical applications such as application of the hemostatic device by a digit, suturing the hemostatic device, applications of the hemostatic device in the form of a tampon, balloon, clip, or other forms of topical dressings such as bandages. The hemostatic device described above may be applied to the anatomic site requiring hemostasis in the form of a gel, glue, foam, or spray.

A tampon, cylindrical shape, or conical shape may be made by selectively shaping the wafer described above. Shaping may be accomplished mechanically by cutting/carving a wafer to a desired shape. Alternatively, the wafer is made into specific tampon-shapes by specific shaped molds to compress them into. The tampon hemostatic device embodiment is introduced into the anatomic site requiring hemostasis by manual or instrument introduction. Non-limiting examples of sites and applications where the tampon hemostatic device according to the invention may be useful are lumpectomy sites, tumor removal sites, tissue voids due to trauma or tissue/organ excision, organ hemorrhage locations, puncture wounds, dental alveolus, urethra, vagina, nasal cavity, nasal sinus, vessels, intramedullary cavity and head wounds.

A balloon hemostatic device may be made by shaping the sheet form of an ECM into an expandable balloon, pressing the wafer form described above as an external sheet onto the outside of the sheet, and then deflating the balloon to allow for minimally invasive delivery. In one embodiment the exterior surface of the balloon is coated with an ECM gel, powder, foam or wafer-like compressed powder, for example. The balloon embodiment of the hemostatic device could then be inserted into a tissue defect at an anatomical site in a patient. The balloon is filled with a substance to expand the balloon so that the external wafer sheet component is pressed into contact with the tissue defect at the anatomical site in the patient. The balloon itself performs as the sheet material that provides a physical barrier to unimpeded blood flow through the hemostatic device.

In one embodiment, the balloon is filled with saline or contrast material for imaging purposes. Alternatively, the balloon is filled with an ECM gel or ECM paste that would induce total construct remodeling into host tissue at the anatomic site where the balloon is inflated.

Non-limiting examples of hemostatic sites and applications where the balloon hemostatic device may be useful are internal bleeding sites accessed by minimally invasive procedures, internal bleeding sites accessed laparoscopically, puncture wounds, thoracic cavity, abdominal cavity, pulmonary or hepatic lobectomy, vagina, urethra, uterus, pelvic cavity, urinary bladder, subcutaneous tissue, and between a topical dressing and an open wound such as a crushing wound.

In another embodiment of the hemostatic device of the invention, a clip is made by external fixation of the wafer/sheet construct over an anatomical site, for example using it as a staple bolster device where the wafer/sheet construct is a continuous piece that is wrapped over an anastomosis site, such as anastomosis of intestinal segments, or two wafer/sheet devices are used on top or bottom or two sides, and an external clip or staple is used to fix and compress the device at the site.

In another embodiment of the invention, a spray is made from the ECM gel hemostatic device described above or from an ECM particulate paste hemostatic device that is sprayed onto an anatomic site requiring hemostasis. ECM gel form or ECM particulate paste form is loaded into a delivery system that can be introduced by minimally invasive procedures. The final delivery of the hemostatic device is achieved by pressure or physical advancement of the ECM material through a sheath, syringe, or nozzle such that the ECM gel hemostatic device or ECM particulate paste hemostatic device is applied at the desired site. Spray width and area can be controlled by the size of the opening of the sheath, syringe, or nozzle.

Another embodiment of the invention is directed to a gel that expands in vivo when injected into a site and occupying space and achieving hemostasis. Another embodiment of the invention is directed to a gel that would polymerize in vivo. When the polymerizable gel hemostatic device is injected into a site, it polymerizes and stays fixed in position to achieve hemostasis. Gel form ECM materials can polymerize after a change in pH. Once the polymerizable gel hemostatic device is introduced into the desired site, the pH at the site can be altered by an addition of an acid or base enabling the gel to polymerize in vivo at the application site. Gel form material can also polymerize at body pH after application to the desired site.

Typically, to make the hemostatic device according to the invention, the ECM particulate material, for example, UBM particulate material, is rehydrated in water and pressed into a pre-made polymer mold, e.g., a Porex (Porex Corporation, 500 Bohannon Road, Fairburn, Ga. 30213 USA) plastic mold and dehydrated by compression, vacuum, heat, or lyophilization. The molds are sized and shaped for the intended purpose of the hemostatic device. For example, but not limited to, hemostatic device shapes are wafer-, rectangular-, oval-, teardrop-, round-, cylindrical-, conical-, or a site-specific-shape to fit the anatomy of the anatomic site where the hemostatic device is to be applied to induce hemostasis. Such internal and external anatomical sites include, for example, but are not limited to skin puncture wounds, other skin wounds such as lacerations or incisions, abdominal wounds, thoracic wounds, wounds to abdominal or thoracic organs, head wounds including wounds to the brain or skull, skeletal fractures, extremity wounds due to trauma or amputation, organ tumor removal or diseased tissue removal/excision, and internal application into a blood vessel in a non-compressible area that feeds a bleeding site.

The hemostatic devices according to the invention have varying densities ranging from about 10 mg/cm$^3$ to about 600 mg/cm$^3$, preferably about 15 mg/cm$^3$ to about 450 mg/cm$^3$, more preferably about 20 mg/cm$^3$ to about 300 mg/cm$^3$.

The density of the hemostatic device may be varied by one of at least two methods. In one embodiment, the amount of rehydration fluid, for example, saline, Ringer's solution, or purified water, that is mixed with a fixed amount of particulate ECM product is set to achieve a predetermined density of the hemostatic device. Alternatively, in another embodiment, the amount of particulate product is pre-set to achieve a predetermined density when mixed with a fixed amount of rehydration fluid. Alternatively, the density can be varied by the amount of external compression during drying, the magnitude of vacuum applied, changing the flexibility of the silicone membrane used to pull down over it, and by compressing in a rigid non-compressible mold/covering.

The rehydrated particulate ECM product is then pressed into a mold. In one embodiment, a hydrated backing sheet or multiple backing sheet layers of hydrated ECM, UBM, for example, are placed on top of the rehydrated particulate ECM product that was pressed into the mold. The rehydrated product that is pressed into the mold may be dehydrated by mechanical compression to form the wafer or to form other shapes of the hemostatic device, Optionally, mechanical compression is combined with heat and/or vacuum to dehydrate the molded particulate product. As the particulate ECM product is dehydrated, the backing sheets of ECM placed in contact with the particulate ECM product adhere to the particulate ECM material. Alternatively, adherence may be accomplished by adhesives or mechanical fixation, e.g. sutures.

In a particular embodiment for making the hemostatic device according to the invention, a sheet of a material (e.g. porous polyethylene), Porex, for example, is placed over and in contact with the backing sheets of ECM material in contact with the particulate ECM material while the particulate ECM material and the backing ECM sheet are being dehydrated. The sheet of Porex uniformly applies compression, heat, and/or vacuum to the molded particulate ECM product to avoid achieving an undesired or uneven density of the final product, i.e., the final hemostatic device.

After dehydration has achieved the desired level, the hemostatic device is sterilized by, for example, radiation (e-beam, gamma) or gas (ethylene oxide or nitric dioxide).

EXAMPLES

Figure 2:
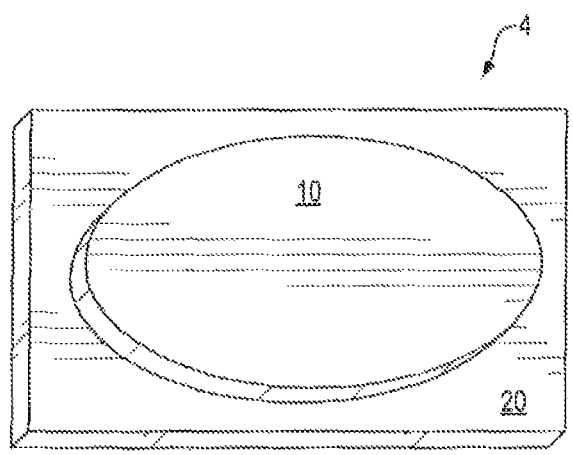
FIG. 2 illustrates a perspective view of the hemostatic device according to another embodiment of the invention.

A lyophilized UBM powder was rehydrated (400 mg/ml) in WFI (water for irrigation), compressed into 2 cm×2 cm×4 mm wafers, and dehydrated under vacuum. Referring to FIG. 1, a portion of the wafers were backed with a backing sheet of two layer-UBM as described above. Referring to FIG. 2, the remaining wafers did not have a backing.

A study was done on the initiation and acceleration of hemostasis using the backed wafer and the non-backed wafer according to the invention described above compared to other hemostatic materials. A porcine non-coagulopathic liver hemorrhage model was used for this study. Four millimeter biopsy punches were used to create 8 mm-deep wounds in the exteriorized liver of a pig. Following 15 seconds of bleeding, the wounds were wiped and UBM wafers, size-matched Hemcon chitosan bandage (Kytostat), or Surgicel ORC hemostat (4-layers, Ethicon) were randomized to injury (N=4 ea), applied to the bleeding anatomical site on the liver surface and held under constant digital pressure for 30 seconds. Hemostasis was assessed at these sites and at a suitable control site where a hemostatic device was not applied at 30 seconds and at 30 second intervals thereafter.

Figure 3:
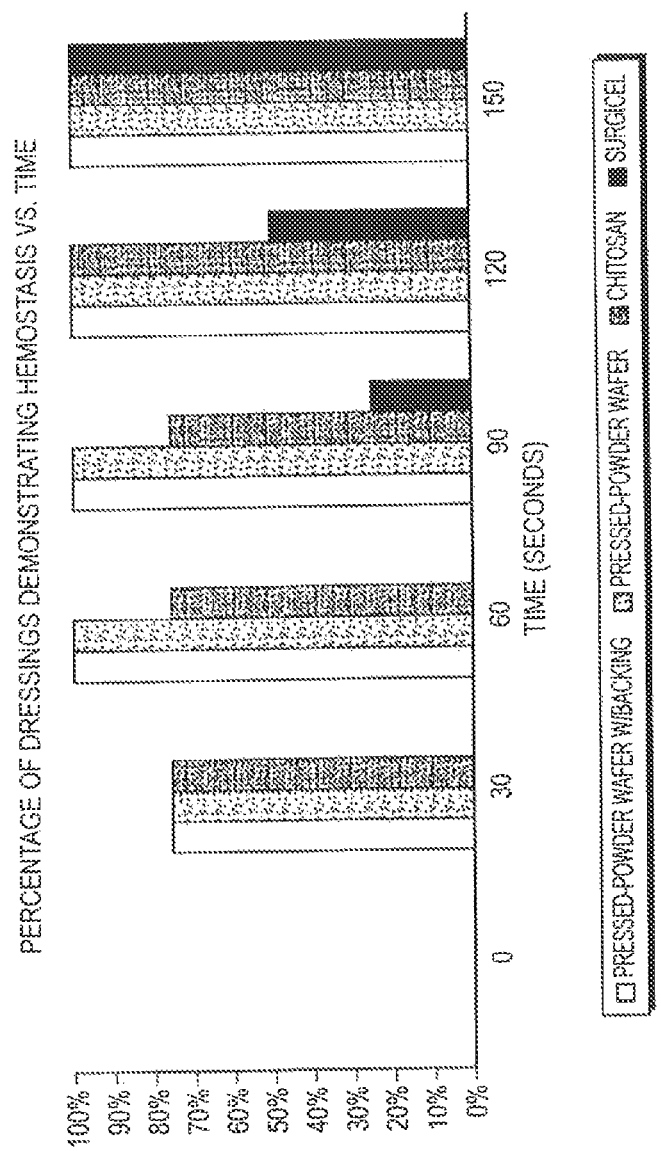
FIG. 3 illustrates in graphic a comparison of the percentage of UBM hemostatic devices without an ECM backing, the percentage of UBM hemostatic devices with an ECM backing, the percentage of Hemcon chitosan dressings, and the percentage of Surgicell dressings that demonstrate hemostasis at 30, 60, 90, 120 and 150 minutes after application in a porcine liver hemorrhage model.

Referring to FIG. 3, all of the UBM wafers, backed and non-backed, achieved hemostasis at 60 seconds, all of the KytoStat dressings achieved hemostasis at 120 seconds and all of the Surgicel devices achieved hemostasis at 150 seconds. There was a noted delay in onset of hemostasis for Surgicel due to upwelling of blood from the injury through the very porous Surgicel fabric, compared to the other dressings. Both the chitosan and UBM wafers began to achieve hemostasis at 30 seconds. Hemostasis was not achieved at the control site during the time periods evaluated.

In another aspect, the invention is a method of applying the hemostatic device described above to a topical internal or external site of a patient to induce and accelerate hemostasis.

In one embodiment of this aspect of the invention, the hemostatic device is placed over a bleeding vessel on the surface of a bleeding tissue. The bleeding tissue may be external such as on the skin or on the exposed ends of a bone in a compound fracture. Alternatively, the bleeding tissue is internal, for example, intracranial, intrathecal, intraabdominal, intrathoracic, intramedullary, intramuscular, intrauterine, intravaginal, or from lung, spleen, liver, or kidney.

In a particular embodiment, the gel form or the tampon form of the hemostatic device could be applied into the lumen of a bleeding vessel.

In a particular embodiment of the invention, the hemostatic device is placed on the surface of the bleeding tissue and held in place with digital pressure, or with a dressing, sutures, clip or tissue glue, for example.

In yet another embodiment of the invention, the hemostatic device is a tampon that is inserted into a bleeding orifice such as the cervix, vagina, uterus, nasal passage, tooth socket, or ear canal. Alternatively, the hemostatic device is applied to the surface of an inflatable balloon, inserted into an anatomical opening or anatomical space, for example the lumen of an organ such as the urinary bladder, and inflated to fill the space.

In another embodiment, the hemostatic device is a wafer with a sheet backing as described above and sized and shaped to fit the target internal anatomical site requiring hemostasis. For example, in a tumor resection of an internal tissue, the hemostatic device is an oblong tapering wafer component with a disc or oval sheet backing, similar to the tampon, cylindrical shape, or conical shape design described above so that the device can be inserted into the tumor resection site to induce and accelerate hemostasis while simultaneously providing an ECM scaffold for site specific remodeling. For example, the hemostatic device could be made with a larger size wafer and sheet backing for application to a lung remnant after a partial lobectomy so that the hemostatic device accelerates hemostasis and provides a leak-proof seal. Alternatively, the hemostatic device is thimble or bowl-shaped where the wafer component is hemispherical with or without an external sheet backing for hemostasis applications to a liver or kidney after a hepatic lobectomy or partial nephrectomy, respectively.

In still another embodiment of the invention, the hemostatic device comprises a gel or foam and is injected onto the surface of a bleeding tissue or injected into the orifice of a bleeding anatomical site to induce hemostasis. Additionally, the hemostatic device according to the invention can be sprayed on a surface to treat, for example, muscular, retroperitoneal, peritoneal, pleural or pericardial bleeding.

Variations, modifications, and other implementations of what is described herein will occur to those of ordinary skill in the art without departing from the spirit and scope of the invention as claimed. Accordingly, the invention is to be defined not by the preceding illustrative description but rather by the spirit and scope of the following claims.

Each of the references provided herein are incorporated by reference in their entirety.

What is claimed is:

1. A method for manufacturing a material for assisting hemostasis, comprising:
    rehydrating a particularized dehydrated extracellular matrix (ECM) material derived from an epithelial tissue comprising non-cross linked ECM components, said ECM material further comprising epithelial basement membrane and consisting of one or more layers selected from the group consisting of tunica propria, tunica muscularis mucosa, tunica submucosa, and tunica muscularis; and,
    compressing said rehydrated material under a vacuum to form a dehydrated wafer.

2. The method of claim 1 wherein said ECM further comprises tunica propria.

3. The method of claim 1 wherein said ECM further comprises submucosa.

4. The method of claim 1 wherein said ECM further comprises tunica muscularis.

5. The method of claim 1 wherein said epithelial basement membrane is free of epithelial cells and epithelial cellular components.

6. The method of claim 1 wherein said material for assisting hemostasis further comprises applying a backing sheet of ECM to said wafer.

7. The method of claim 1 wherein said method excludes the step of applying cross-linkers to said ECM material at any stage of manufacture.

8. The method of claim 1 further comprising forming a plurality of ECM layers and particularizing the plurality of ECM layers before rehydrating the particularized ECM material.

9. The method of claim 1 wherein said ECM further comprises tunica muscularis mucosa.

10. The method of claim 1 wherein said non-cross-linked components are selected from the group consisting of collagen type IV, collagen type VII, glycosaminoglycans, fibronectin, and laminin.

11. The method of claim 10 wherein said cross-linked component comprises type VII collagen.

12. The method of claim 1 wherein said material is sized and shaped for introduction into one of the group consisting of uterus, medullary cavity, nasal passage, nasal sinus, auditory canal, cervix, and tooth socket.

13. The method of claim 1 wherein said material is sized and shaped for introduction into one of the group consisting of abdomen, thorax, cranium, urethra, vagina, nasal cavity, nasal sinus, vessel, intramedullary cavity, uterus, head structures, eye, dental alveolus, lung, liver, pelvic cavity, urinary bladder, subcutaneous tissue, muscle, organ resection sites, tissue resection sites, auditory canal, and percutaneous puncture wounds.

14. The method of claim 6 wherein said backing sheet is applied to said wafer while said rehydrated ECM is being dehydrated.

15. The method of claim 1 wherein said ECM is derived from the urinary bladder.

16. The method of claim 14 wherein said applied backing comprises at least two sheets of ECM.

* * * * *